United States Patent
Farber et al.

(10) Patent No.: US 11,667,883 B2
(45) Date of Patent: Jun. 6, 2023

(54) MICROBIOLOGICAL MEDIA AND METHODS OF USING SAME

(71) Applicant: Saint Joseph's University, Philadelphia, PA (US)

(72) Inventors: Matthew J. Farber, Media, PA (US); Pham Kent, Buena Park, CA (US)

(73) Assignee: Saint Joseph's University, Philadelphia, PA (US)

( * ) Notice: Subject to any disclaimer, the term of this patent is extended or adjusted under 35 U.S.C. 154(b) by 0 days.

(21) Appl. No.: 16/977,950

(22) PCT Filed: Mar. 5, 2019

(86) PCT No.: PCT/US2019/020822
§ 371 (c)(1),
(2) Date: Sep. 3, 2020

(87) PCT Pub. No.: WO2019/173389
PCT Pub. Date: Sep. 12, 2019

(65) Prior Publication Data
US 2021/0040437 A1      Feb. 11, 2021

Related U.S. Application Data

(60) Provisional application No. 62/714,283, filed on Aug. 3, 2018, provisional application No. 62/639,433, filed on Mar. 6, 2018.

(51) Int. Cl.
*C12N 1/04*     (2006.01)
*C12N 1/18*     (2006.01)

(52) U.S. Cl.
CPC ............... *C12N 1/04* (2013.01); *C12N 1/18* (2013.01); *C12N 2500/20* (2013.01); *C12N 2500/34* (2013.01)

(58) Field of Classification Search
None
See application file for complete search history.

(56) References Cited

U.S. PATENT DOCUMENTS

| 5,534,415 A | 7/1996 | Orenga |
| 2007/0218521 A1 | 9/2007 | De Caux |
| 2016/0060678 A1 | 3/2016 | Vágvölgyi et al. |

FOREIGN PATENT DOCUMENTS

WO     2016164223 A1     10/2016

OTHER PUBLICATIONS

Flückiger-Isler, Rosina, et al. "Dietary components of malt extract such as maltodextrins, proteins and inorganic salts have distinct effects on glucose uptake and glycogen concentrations in rats." The Journal of nutrition 124.9 (1994): 1647-1653. (Year: 1994).*
De Figueroa, L. I., M. F. De Richard, and M. R. de Van Broock. "Interspecific protoplast fusion of the baker's yeast *Saccharomyces cerevisiae* and *Saccharomyces diastaticus*." Biotechnology letters 6.4 (1984): 269-274. (Year: 1984).*
"YPD Broth (YEPD Broth)", HiMedia Laboratories, Version 2015. Retrieved Apr. 24, 2019 @ www.himedialabs.com/TDZM1363.pdf, 2015.
Andrews, et al., "Super-Attenuation of Beer: A Study of Three Organisms Capable of Causing Abnormal Attenuations", J Inst Brew, vol. 58, 1952, pp. 189-196.
Lin, "Formulation and Testing of Cupric Sulphate Medium for Wild Yeast Detection", J Inst Brew, vol. 87, 1981, pp. 151-154.
International Search Report dated May 28, 2019 for corresponding PCT International Application No. PCT/US19/20822.

* cited by examiner

*Primary Examiner* — Robert J Yamasaki
(74) *Attorney, Agent, or Firm* — Saul Ewing LLP; Domingos J. Silva; Chihao Wang (57) ABSTRACT

The present invention relates to the unexpected discovery of a novel yeast culture medium comprising a concentration of cupric sulfate sufficient to promote growth of strains of *Saccharomyces cerevisiae* var. *diastaticus* while inhibiting growth of other varieties of brewing yeast. In certain embodiments, the invention provides a yeast culture medium. In other embodiments, the invention provides methods of using the novel yeast culture medium to test yeast slurries for contamination with *Saccharomyces cerevisiae* var. *diastaticus*.

21 Claims, 10 Drawing Sheets

| Strain name | Source | LCSM growth | CSSM growth |
|---|---|---|---|
| BY1 | WLP565 – Belgian Saison I | Yes | Yes |
| BY2 | WLP566 – Belgian Saison II | Negative | Yes |
| BY3 | WLP099 – Super High Gravity Ale | Yes | Yes |
| BY4 | WLP545 – Belgian Strong Ale | Variable | Yes |
| BY5 | WLP550 – Belgian Ale | Negative | Negative |
| BY6 | WLP570 – Belgian Golden Ale | Yes | Yes |
| BY7 | WLP590 – French Saison Ale | Yes | Yes |
| BY8 | WLP351 – Bavarian Weizen | Negative | Yes |
| BY9 | WLP644 – S. Bruxellensis Trois | Variable | Yes |
| BY10 | Belle Saison - Lallemand | Yes | Yes |
| DB-A | Isolated from local brewery | Yes | Yes |
| DB-B | Isolated from local brewery | Yes | Yes |
| Y-2416 | ATCC 13007 (*diastaticus*) | Yes | Yes |
| YB-4328 | IFO 1046 (*diastaticus*) | Yes | Yes |
| BY11 | WLP002 – English Ale | Negative | Negative |
| BY12 | WLP013 – London Ale | Negative | Negative |
| Y-123 | ATCC 2335 (*S. cerevisiae*) | Negative | Negative |

FIG. 7

| Strain name | Source | *STA1* (brewSTAT) | Sporulation (n > 100) | *Over-attenuation* |
|---|---|---|---|---|
| BY1 | WLP565 – Belgian Saison I | Yes | 4% | Yes |
| BY2 | WLP566 – Belgian Saison II | Yes | 54% | Negative |
| BY3 | WLP099 – Super High Gravity Ale | Yes | 7% | Yes |
| BY4 | WLP545 – Belgian Strong Ale | Yes | Negative | Negative |
| BY5 | WLP550 – Belgian Ale | Negative | 29% | Negative |
| BY6 | WLP570 – Belgian Golden Ale | Yes | 6% | Negative |
| BY7 | WLP590 – French Saison Ale | Yes | Negative | Yes |
| BY8 | WLP351 – Bavarian Weizen | Yes | 13% | Negative |
| BY9 | WLP644 – S. Bruxellensis Trois | Yes | 1% | Negative |
| BY10 | Belle Saison – Lallemand | Yes | Negative | Yes |
| DB-A | Isolated from local brewery | Negative | 51% | Negative |
| DB-B | Isolated from local brewery | Yes | 10% | Yes |
| Y-2416 | ATCC 13007 (*diastaticus*) | Yes | Negative | Yes |
| YB-4328 | IFO 1046 (*diastaticus*) | Negative | 72% | Negative |
| BY11 | WLP002 – English Ale | Negative | Negative | Negative |
| BY12 | WLP013 – London Ale | Negative | Negative | Negative |
| Y-123 | ATCC 2335 (*S. cerevisiae*) | Negative | Negative | Negative |

FIG. 8

DB-A: Brewery isolate

Y-123: *S. cerevisiae*

FIG. 9

| Isolate | Source | STA1 (brewSTAT) | LCSM Growth | CSSM Growth | Sporulation | Over-attenuation |
|---|---|---|---|---|---|---|
| Isolate #1 | Yeast slurry | Yes | Negative | Yes | Negative | Negative |
| Isolate #2 | Unfiltered beer | Yes | Negative | Yes | Negative | Negative |
| Isolate #3 | Finished beer #1 | Yes | Negative | Yes | Negative | Negative |
| Isolate #4 | Finished beer #2 | Yes | Yes | Yes | Negative | Negative |
| Isolate #5 | Isolated yeast from beer #2 | Yes | Yes | Yes | Negative | Negative |

MICROBIOLOGICAL MEDIA AND METHODS OF USING SAME

CROSS-REFERENCE TO RELATED APPLICATIONS

The present application is a 35 U.S.C. § 371 national phase application from, and claims priority to, PCT International Patent Application No. PCT/US2019/020822, filed Mar. 5, 2019, which claims priority under 35 U.S.C. § 119(e) to U.S. Provisional Applications No. 62/639,433, filed Mar. 6, 2018, and No. 62/714,283, filed Aug. 3, 2018, all of which applications are incorporated herein by reference in their entireties.

BACKGROUND OF THE INVENTION

*Saccharomyces cerevisiae* var. *diastaticus*, hereby called *diastaticus*, is a subspecies of the common brewer's yeast *Saccharomyces cerevisiae*. That subspecies is capable of fermenting starch and dextrin. Some *diastaticus* strains are true wild yeast contaminants, but other strains have been selected and marketed as saison ale strains, noted for very high attenuation rates and phenolic profile during beer fermentation. These strains are commonly found as contaminants in over-attenuated beer. The diastase activity of *diastaticus* and related beer-spoilage potential are caused by the secretion of a glucoamylase that breaks down dextrins and starch into fermentable sugar. Contamination and re-fermentation in unfiltered, packaged products can lead to ruptured cans or bottles due to overcarbonation, changes in flavor (phenolic off-flavor), and increases in alcohol by volume (ABV) above that which may be legally permissible. Several recent, costly product recalls in the brewing industry have been the result of *S. cerevisiae* var. *diastaticus* contamination.

There is thus a need in the art for compositions and methods of detecting *diastaticus* contamination. In certain embodiments, the compositions and methods would allow for detection of very small amounts *diastaticus* yeast strains when mixed with large amounts of more common brewer's yeast strains. The present invention addresses these needs.

BRIEF SUMMARY OF THE INVENTION

The present invention provides a yeast culture medium comprising a concentration of cupric sulfate and a concentration of starch that promotes growth of strains of *Saccharomyces cerevisiae* var. *diastaticus* while inhibiting growth of other varieties of brewing yeast. Non-limiting examples of the inhibited varieties of brewing yeast include, but are not limited to, *Saccharomyces cerevisiae*, *Saccharomyces pastorianus*, *Brettanomyces bruxellensis*, *Brettanomyces claussenii*, *Brettanomyces lambicus*, and *Brettanomyces anomalus*.

In certain embodiments, the yeast culture medium comprises yeast extract. In certain embodiments, the yeast culture medium comprises peptone. In certain embodiments, the yeast culture medium comprises cupric sulfate. In certain embodiments, the yeast culture medium comprises potassium phosphate. In certain embodiments, the yeast culture medium comprises ammonium chloride. In certain embodiments, the yeast culture medium comprises water. In certain embodiments, the yeast culture medium comprises starch. In certain embodiments, the yeast culture medium comprises dextrin. In certain embodiments, the yeast culture medium further comprises agar. In certain embodiments, the yeast culture medium further comprises at least one strain of *Saccharomyces cerevisiae*.

The present invention further provides methods for testing beer for contamination with *Saccharomyces cerevisiae* var. *diastaticus*. In certain embodiments, the invention provides methods of using the novel yeast culture medium to test yeast slurries for contamination with *Saccharomyces cerevisiae* var. *diastaticus*.

BRIEF DESCRIPTION OF THE DRAWINGS

The following detailed description of specific embodiments of the invention will be better understood when read in conjunction with the appended drawings. For the purpose of illustrating the invention, the drawings illustrate specific embodiments. It should be understood, however, that the invention is not limited to the precise arrangements and instrumentalities of the embodiments shown in the drawings.

DETAILED DESCRIPTION OF THE INVENTION

The present invention relates to the unexpected discovery of a novel yeast culture medium comprising a concentration of cupric sulfate and a concentration of starch that promotes growth of strains of *Saccharomyces cerevisiae* var. *diastaticus* while inhibiting growth of other varieties of brewing yeast such as *Saccharomyces cerevisiae, Saccharomyces pastorianus, Brettanomyces bruxellensis, Brettanomyces claussenii, Brettanomyces lambicus*, and *Brettanomyces anomalus*.

In certain embodiments, the inhibited brewing yeast comprises *Saccharomyces cerevisiae*. In certain embodiments, the inhibited brewing yeast comprises *Saccharomyces pastorianus*. In certain embodiments, the inhibited brewing yeast comprises *Brettanomyces bruxellensis*. In certain embodiments, the inhibited brewing yeast comprises *Brettanomyces claussenii*. In certain embodiments, the inhibited brewing yeast comprises *Brettanomyces lambicus*. In certain embodiments, the inhibited brewing yeast comprises *Brettanomyces anomalus*.

In certain embodiments, the invention provides a yeast culture medium. In certain embodiments, the invention provides methods for testing beer for contamination with *Saccharomyces cerevisiae* var. *diastaticus*. In other embodiments, the invention provides methods of using the novel yeast culture medium to test yeast slurries for contamination with *Saccharomyces cerevisiae* var. *diastaticus*.

Definitions

As used herein, each of the following terms has the meaning associated with it in this section.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

Generally, the nomenclature used herein and the laboratory procedures in yeast culturing and beer brewing are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following abbreviations are used herein: ABV, Alcohol by Volume; CSSM, Cupric Sulfate Starch Medium; LCSM, Lin's Cupric Sulfate Medium; PCR, polymerase chain reaction; YPD, yeast extract peptone dextrose.

Compositions

In one aspect, the invention provides a yeast culture medium composition comprising a concentration of cupric sulfate that promotes growth of *Saccharomyces cerevisiae* var. *diastaticus* while inhibiting growth of other varieties of brewing yeast such as *Saccharomyces cerevisiae, Saccharomyces pastorianus, Brettanomyces bruxellensis, Brettanomyces claussenii, Brettanomyces lambicus*, and *Brettanomyces anomalus*.

In another aspect, the invention provides a yeast culture medium composition comprising a concentration of carbohydrate such as starch or dextrin that promotes growth of *Saccharomyces cerevisiae* var. *diastaticus* while inhibiting growth of other varieties of brewing yeast such as *Saccharomyces cerevisiae, Saccharomyces pastorianus, Brettanomyces bruxellensis, Brettanomyces claussenii, Brettanomyces lambicus*, and *Brettanomyces anomalus*.

In certain embodiments, the composition comprises yeast extract, peptone, starch, cupric sulfate, potassium phosphate, ammonium chloride and water. In other embodiments, the composition further comprises agar. In yet other embodiments, starch is the sole carbon source in the composition. In yet other embodiments, starch is not the sole carbon source in the composition.

In certain embodiments, the medium composition of the invention allows for growth of a *diastaticus* strain in aerobic conditions.

In certain embodiments, the medium composition of the invention allows for growth of a *diastaticus* strain in about 48-72 hours at about 28° C. in aerobic conditions.

In certain embodiments, the medium composition of the invention allows for growth of a *diastaticus* strain in about 48, 50, 52, 54, 56, 58, 60, 62, 64, 66, 68, 70, or 72 hours at about 28° C. in aerobic conditions.

In certain embodiments, the medium composition of the invention allows for growth of a *diastaticus* strain in less than about 72 hours at about 28° C. in aerobic conditions.

In certain embodiments, the medium composition of the invention allows for growth of a *diastaticus* strain in about 48-72 hours at about room temperature in aerobic conditions.

In certain embodiments, the medium composition of the invention allows for growth of a *diastaticus* strain in less than about 72 hours at about room temperature in aerobic conditions.

In certain embodiments, the medium composition of the invention allows for growth of a *diastaticus* strain in about 48, 50, 52, 54, 56, 58, 60, 62, 64, 66, 68, 70, or 72 hours at about room temperature in aerobic conditions.

In certain embodiments, the composition comprises about 2 g/L to about 10 g/L of yeast extract. In other embodiments, the composition comprises about 5 g/L to about 20 g/L of peptone. In yet other embodiments, the composition comprises about 2 g/L to about 20 g/L of starch. In yet other embodiments, the composition comprises about 0.1 g/L to about 4 g/L of cupric sulfate. In yet other embodiments, the composition comprises about 1.8 g/L of cupric sulfate. In yet other embodiments, the composition comprises about 1.0 g/L to about 1.5 g/L of potassium phosphate. In yet other embodiments, the composition comprises about 1.1 g/L of potassium phosphate. In yet other embodiments, the composition comprises about 0.1 g/L to about 1 g/L of ammonium chloride. In yet other embodiments, the composition comprises about 5 g/L to about 30 g/L of agar.

In certain embodiments, the composition comprises about 10 g/L of yeast extract, about 20 g/L of peptone, about 20 g/L of starch, about 1.8 g/L of cupric sulfate, about 1.1 g/L of potassium phosphate, and about 0.5 g/L of ammonium chloride. In yet other embodiments, the composition further comprises about 20 g/L of agar.

In certain embodiments, the yeast extract is autolyzed, dried yeast extract.

In certain embodiments, the composition comprises distilled water. In other embodiments, the composition comprises deionized water. In other embodiments, the composition comprises reverse osmosis water.

In certain embodiments, the composition further comprises at least one buffer selected from the group consisting of Tris(hydroxymethyl)aminomethane (Tris), 3-(N-morpholino) propanesulfonic acid (MOPS), 2-(N-morpholino) ethanesulfonic acid (MES), citrate (sodium citrate and citric acid), acetate (sodium acetate and acetic acid), 4-(2-hydroxyethyl)-1-piperazine ethanesulfonic acid (HEPES), Glycine, and piperazine-N,N'-bis(2-ethanesulfonic acid) (PIPES). In other embodiments, the composition comprises about 5 g/L to about 50 g/L of buffer.

In certain embodiments, the composition comprises an amount of cupric sulfate sufficient to promote growth, propagation or proliferation of *Saccharomyces cerevisiae* var. *diastaticus*. In other embodiments, the composition comprises an amount of cupric sulfate sufficient to inhibit growth, propagation or proliferation of strains of yeast that are not *Saccharomyces cerevisiae* var. *diastaticus*.

In certain embodiments, the composition comprises at least one strain of yeast. In other embodiments, the composition comprises at least one strain of *Saccharomyces cerevisiae*. In yet other embodiments, the composition comprises a strain of *Saccharomyces cerevisiae* var. *diastaticus*.

As demonstrated herein, a *diastaticus* strain can be grown on the culture medium of the invention, which can be used in the brewery for *diastaticus* detection as an agar or broth.

In a non-limiting example, *diastaticus* management in the brewery can involve one or more of the following steps: screen pre-packaged beer via selective media and/or rapid detection (PCR); once the beer is packaged, one should keep samples from each lot in warm and cold storage; $CO_2$ and/or ABV levels should be compared against standards after a determined time in storage; and contamination should be confirmed using selective media and/or PCR tests. Risk associated with contamination can be defined by evaluating characteristics of isolates, such as but not limited to over-attenuation ability, capacity to sporulate, and phenolic off-flavor.

Culturing Methods

The invention further provides methods of culturing yeast on the culture medium composition of the invention. In certain embodiments, the method comprises contacting a yeast sample comprising at least one strain of yeast to the culture medium of the invention and incubating the yeast. In certain embodiments, the sample comprises at least one strain of *Saccharomyces cerevisiae*. In yet other embodiments, the sample comprises at least one strain of *Saccharomyces cerevisiae* var. *diastaticus*.

In certain embodiments, the method comprises culturing the yeast in the medium at a temperature of about 20° C. to about 35° C. In other embodiments, the method comprises culturing the yeast in the medium at a temperature of about 30° C. In other embodiments, the method comprises shaking the medium. In yet other embodiments, the method comprises shaking the medium at a rate of about 180 rpm.

In certain embodiments, the method comprises first propagating the yeast in a first culture medium to form the yeast sample and then contacting the yeast sample to the culture medium composition of the invention. In other embodiments, the first culture medium comprises yeast extract peptone dextrose (YPD). In yet other embodiments, the first culture medium comprises about 2% peptone by weight, about 2% glucose by weight, about 1% yeast extract by weight, and optionally about 2% agar by weight. In certain embodiments, the yeast is propagated in the first culture medium from about 1 to about 2 days. In other embodiments, the yeast is propagated in the first culture medium at a temperature of about 20° C. to about 35° C. In other embodiments, the yeast is propagated in the first culture medium at a temperature of about 30° C.

In certain embodiments, the yeast sample is a yeast slurry. In certain embodiments, the yeast sample is fermenting wort. In certain embodiments, the yeast sample is beer. In certain embodiments, the yeast sample is a malted beverage. In certain embodiments, the yeast sample is an environmental swab.

Screening Methods

The invention further provides a method of identifying presence or absence of *Saccharomyces cerevisiae* var. *diastaticus* in a yeast, beer, malted beverage or fermenting wort sample comprising at least one strain of yeast.

In certain embodiments, the method comprises culturing a yeast sample comprising at least one strain of yeast on the culture medium composition of the invention, wherein if a yeast grows, propagates, and/or proliferates in the culture medium composition of the invention, at least one strain of *Saccharomyces cerevisiae* var. *diastaticus* was present in the sample. In certain embodiments, if no yeast grows, propagates, and/or proliferates in the culture medium composition of the invention, no strains of *Saccharomyces cerevisiae* var. *diastaticus* were present in the yeast sample.

In certain embodiments, the culturing of the yeast sample comprises a yeast culturing method of the invention using a culture medium composition of the invention.

In certain embodiments, the screening method of the invention is useful to determine if a yeast sample is contaminated with *Saccharomyces cerevisiae* var. *diastaticus*. In other embodiments, the screening method of the invention is useful to determine if a beer sample is contaminated with *Saccharomyces cerevisiae* var. *diastaticus*. In other embodiments, the screening method of the invention is useful to prevent contamination of beer with *Saccharomyces cerevisiae* var. *diastaticus*, thereby preventing one or more conditions selected from spoilage, over-fermentation, over-attenuation, over-carbonation, changes in flavor, and/or over-pressurization in the beer.

In certain embodiments, the yeast sample is a yeast slurry. In other embodiments, the yeast sample is derived from a brewed beer. In other embodiments, the yeast sample is derived from an environmental swab.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Medium Formulations

YPD agar comprised 2% peptone, 2% glucose, 1% yeast extract, and 2% agar (Research International Products Corp.). For broth, the agar was omitted. LCSM was created as per the manufacturer's recommendations (Weber Scientific). The recipe for CSSM is listed in Table 1.

TABLE 1

| Cupric Sulfate Starch Media Recipe | |
|---|---|
| Yeast extract | 10 g |
| Peptone | 20 g |
| Agar (Omit if making liquid media) | 20 g |
| Starch | 20 g |
| Cupric Sulfate (Anhydrous) | 1.8 g |
| Dipotassium orthophosphate (potassium phosphate) | 1.1 g |
| Ammonium Chloride | 0.5 g |
| Distilled $H_2O$ | 1000 mL |

Strains Used in this Study

Figure 6:
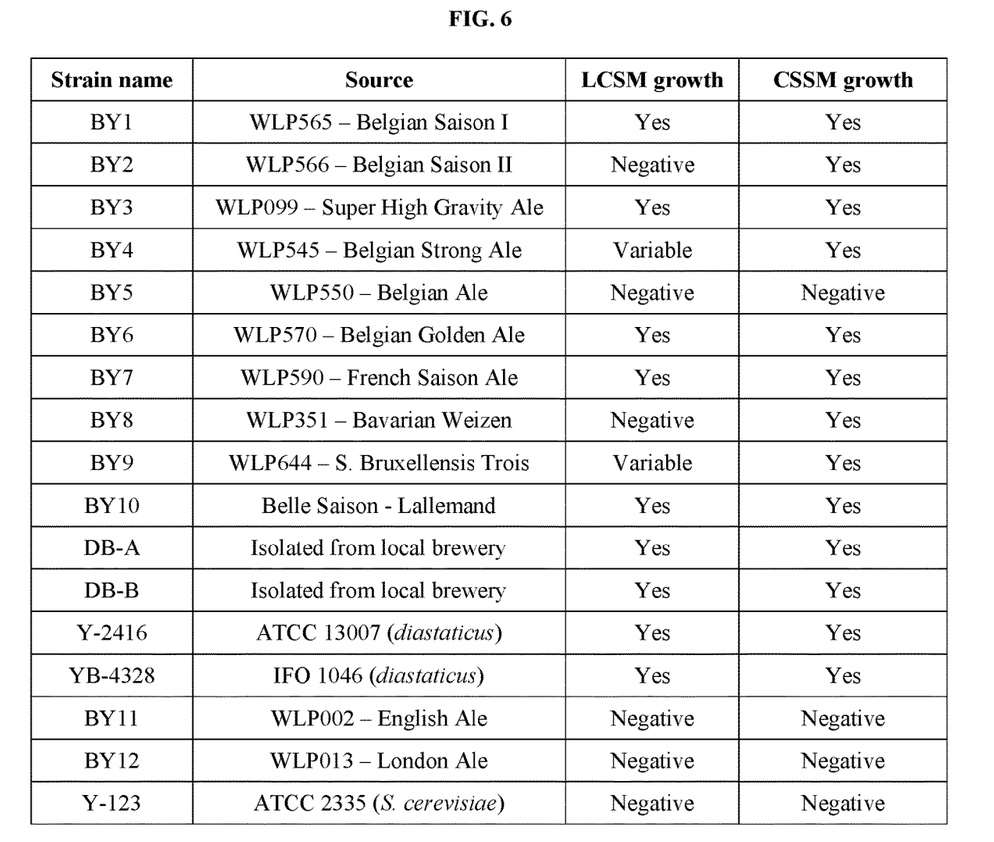
FIG. 6 is a table illustrating strains used and selected results obtained in the present study, comparing growth on LCSM and CSSM.

Three *diastaticus* strains, six *S. cerevisiae* strains, and two unknown wild yeast were used in this study (Table 2). One *diastaticus* strain is commercially sold as a Belgian saison ale, and is labeled "CS1". The other two *diastaticus* strains were derived from yeast banks and were originally isolated from contaminated beer. Of the six *S. cerevisiae* strains, a variety of five commercial ale yeasts were employed along with a single laboratory strain. Also included in this study were two wild yeast strains recently isolated from contaminated, over-attenuated craft beer, DB-A and DB-B, which both tested positive on LCSM at the brewery. A further subset of commercial yeast suspected as *diastaticus* was evaluated in this study (FIG. 6).

TABLE 2

Growth observed after 2 days on CSSM and LCSM plates

| Sample Name | Source | Species | Growth on CSSM | Growth on LCSM |
|---|---|---|---|---|
| DB-A | Brewery | unknown | + | + |
| DB-B | Brewery | unknown | ++ | + |
| CS1 (Belgian Saison Ale) | Commercial Yeast Supplier | *S. cerevisiae* var. *diastaticus* | ++ | + |
| Y-2416 | ATCC 13007 | *S. cerevisiae* var. *diastaticus* | + | − |
| YB-4238 | IFO 1046 | *S. cerevisiae* var. *diastaticus* | + | − |
| Y-123 | ATCC 2335 | *S. cerevisiae* | − | − |
| WLP013 (London Ale) | White Labs | *S. cerevisiae* | − | − |
| WLP002 (English Ale) | White Labs | *S. cerevisiae* | − | − |
| WY1056 (American Ale) | Wyeast | *S. cerevisiae* | − | − |
| WY1272 (American Ale II) | Wyeast | *S. cerevisiae* | − | − |
| WY3068 (Weihenstephan Weizen) | Wyeast | *S. cerevisiae* | − | − |

(+) slow growth;

(++) strong growth;

(−) no growth

Attenuation

Strains used in this study were cultured in yeast extract peptone dextrose (YPD) broth at 30° C. for 2 days. 100 μL of the broth was then added to 10 mL culture media of 50:50 YPD and an American, commercial craft beer. Prior to use, beers were decarbonated by sonication and sterile filtered with a 0.2 μm filter. After another 2 days of growth at 30° C., the culture media was added in a 1:10 volume ratio to each beer. After 7 days of fermentation at 27° C., the density of each sample was measured with a digital densitometer (Metler Toledo).

Culturing

All strains were stored at −80° C. in 10% glycerol. Experiments were conducted with freshly propagated yeast from stocks. All strains were initially cultured on YPD plates at 30° C. for 2 days. Colonies were then sub-cultured onto CSSM and LCSM at 30° C. for 2 days.

PCR

Genomic DNA was extracted via YeaStar Genomic DNA kit (Zymo Research) and diluted to a concentration of <30 ng/μL. PCR was performed with the Phusion Polymerase kit as per manufacturer's instructions (New England Biolabs). The PCR conditions for *diastaticus* detection, the detection of the STA1 gene, was performed as described by Yamauchi et al., 1998, J. Amer. Soc. Brewing Chemists 56(2):58-63. In brief, the SD-5A (CAACTACGACTTCTGTCATA) and SD-6B (GATGGTGACGCAATCACGA) primers were used. The PCR program included an initial 94° C. for 40 sec, then 35 cycles of 94° C. for 20 sec, 54° C. for 30 sec, and 72° C. for 30 sec, followed by 72° C. for 7 min. The products were resolved on a 1% agarose gel and visualized under UV-light. Presence of the STA1 gene was also determined with a BrewSTAT PCR test as per manufacturer's instructions (Invisible Sentinel).

Enrichment and Detection of *diastaticus* in a Yeast Slurry

Freshly cultured *diastaticus* and *S. cerevisiae* (Y-123) cells in YPD broth were counted via hemocytometer and mixed at a cell count ratio of 1:1000 respectively. The mixture was then diluted with YPD to reach a cell count of $1*10^6$ cells per mL and 100 μL of the dilution was then plated onto the CSSM plates and incubated for 2 days at 30° C. Another 100 μL of the diluted cell mixture was added to the CSSM liquid medium and incubated at 30° C., shaking at 180 rpm, for 2 days. After 2 days, 100 μL of the enrichment culture was plated onto CSSM.

Endospore Detection

*Diastaticus* and *S. cerevisiae* strains were streaked onto YPD plates and incubated at 30° C. for 2 days in order to isolate single colonies. Individual colonies were then picked and streaked onto Yeast and mold agar (2% agar, 1% glucose, 0.3% yeast extract, 0.3% malt extract, 0.5% peptone), acetate agar (0.1% glucose, 0.18% potassium chloride, 0.82% sodium acetate trihydrate, 0.25% yeast extract, 1.5% agar), cornmeal agar, V8 juice agar, and malt extract agar (2% agar, 5% powdered malt extract). The plates were then grown for 10 days at ~25° C., out of direct light. Samples were checked on days 3, 5, 7 and 10 for formation of endospores. On day 10, endospores were stained with Malachite Green and counterstained with Safranin-O.

Example 1

Over-Attenuation of Commercial Craft Beer by *diastaticus* Strains

Figure 1:
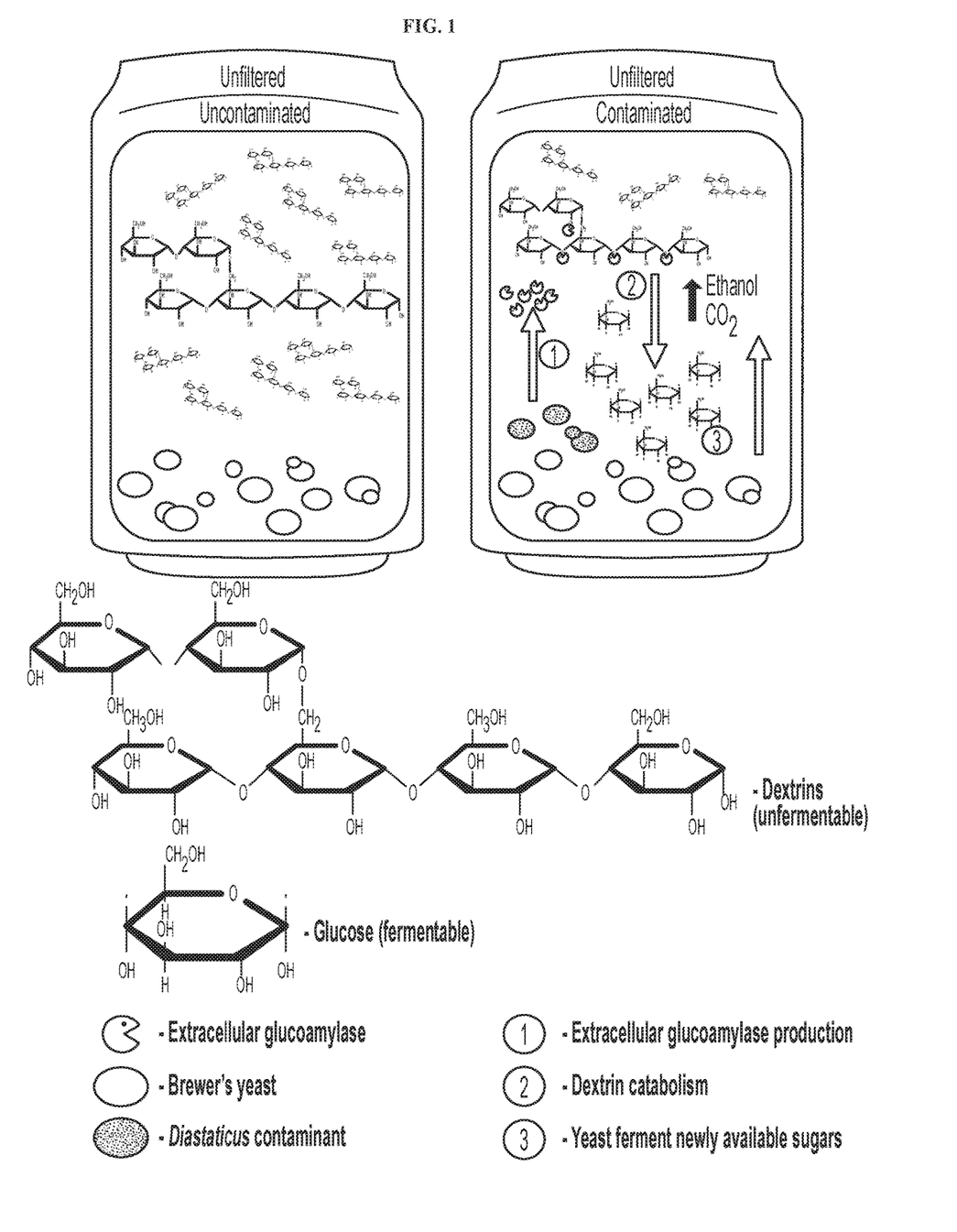
FIG. 1 is a schematic outlining the problems faced during beer brewing when *diastaticus* contamination occurs.
Figure 2A:
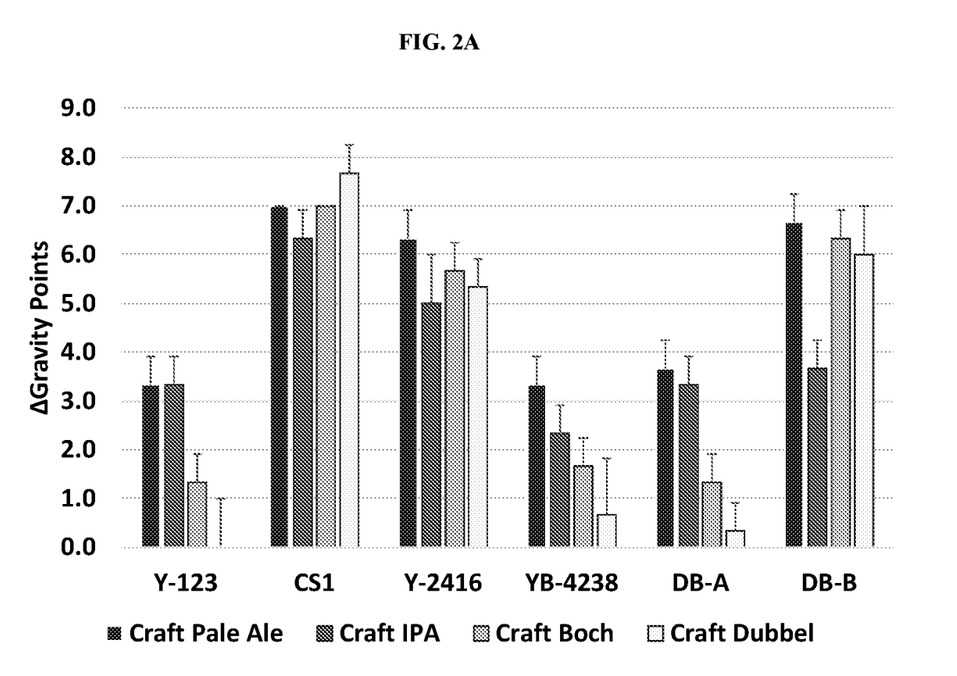
FIGS. 2A-2B are graphs comparing re-fermentation rates of commercial craft beers by *diastaticus*. Several different commercial craft beers (Pale ale, IPA, Boch, and Dubbel) were re-fermented with Y-123, CS1, Y-2416, YB-4238, DB-A, or DB-B. The specific gravity after re-fermentation was subtracted by the specific gravity of the commercial beer to yield the change in Gravity Points. The average of three independent experiments is displayed. Error bars represent the standard deviation.
Figure 2B:
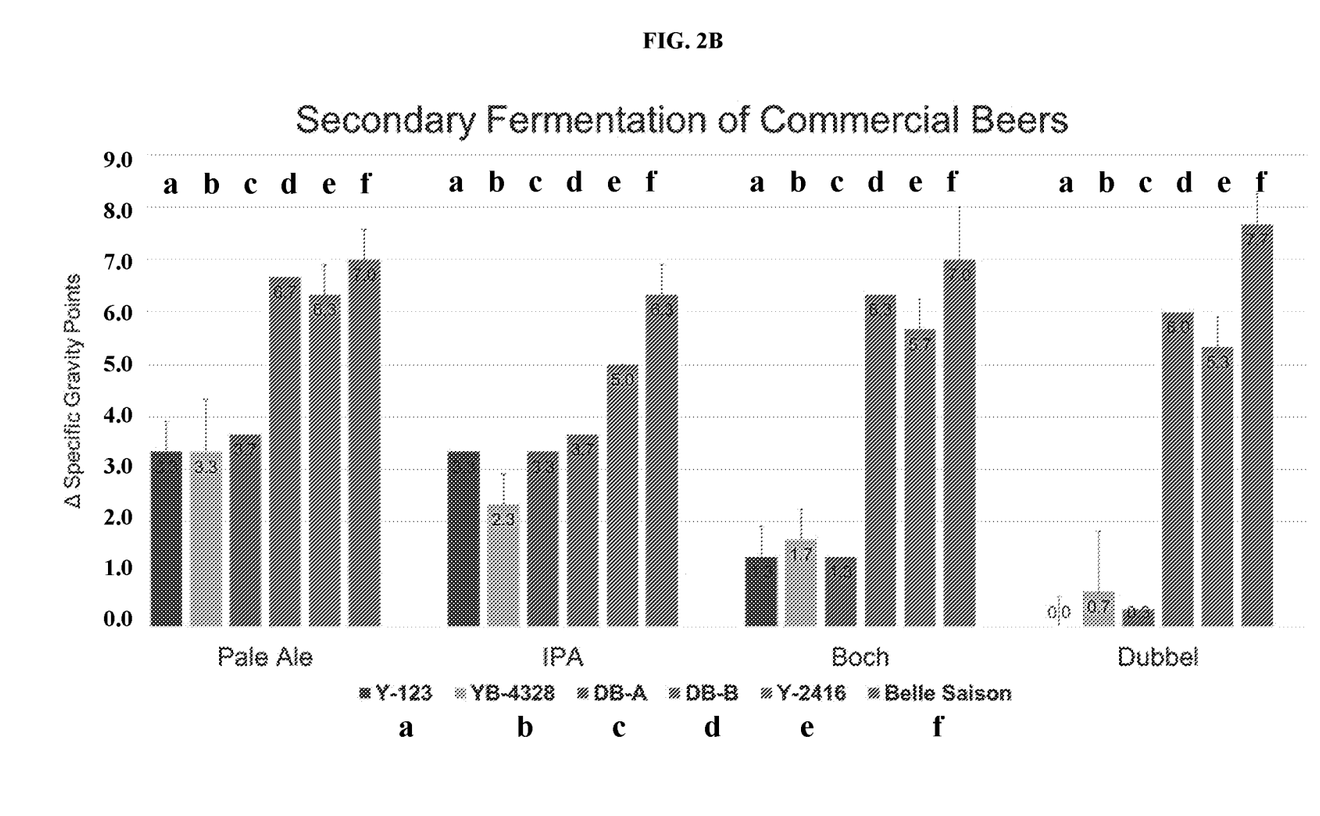

The ability of the *diastaticus* strains to over-attenuate commercial beer was evaluated for four different, American craft beers: a pale ale, an IPA, a Boch, and a Dubbel. The yeast strains were pre-conditioned in a 50:50 mixture of YPD and beer before re-fermentation trials in 100% beer. After 7 days of re-fermentation, specific gravity was measured and the change in specific gravity from the start of re-fermentation was determined (FIGS. 2A-2B). The degree to which each commercial beer was re-fermented varied according to the style and likely reflects the different amounts of residual carbohydrates in each.

Figure 7:
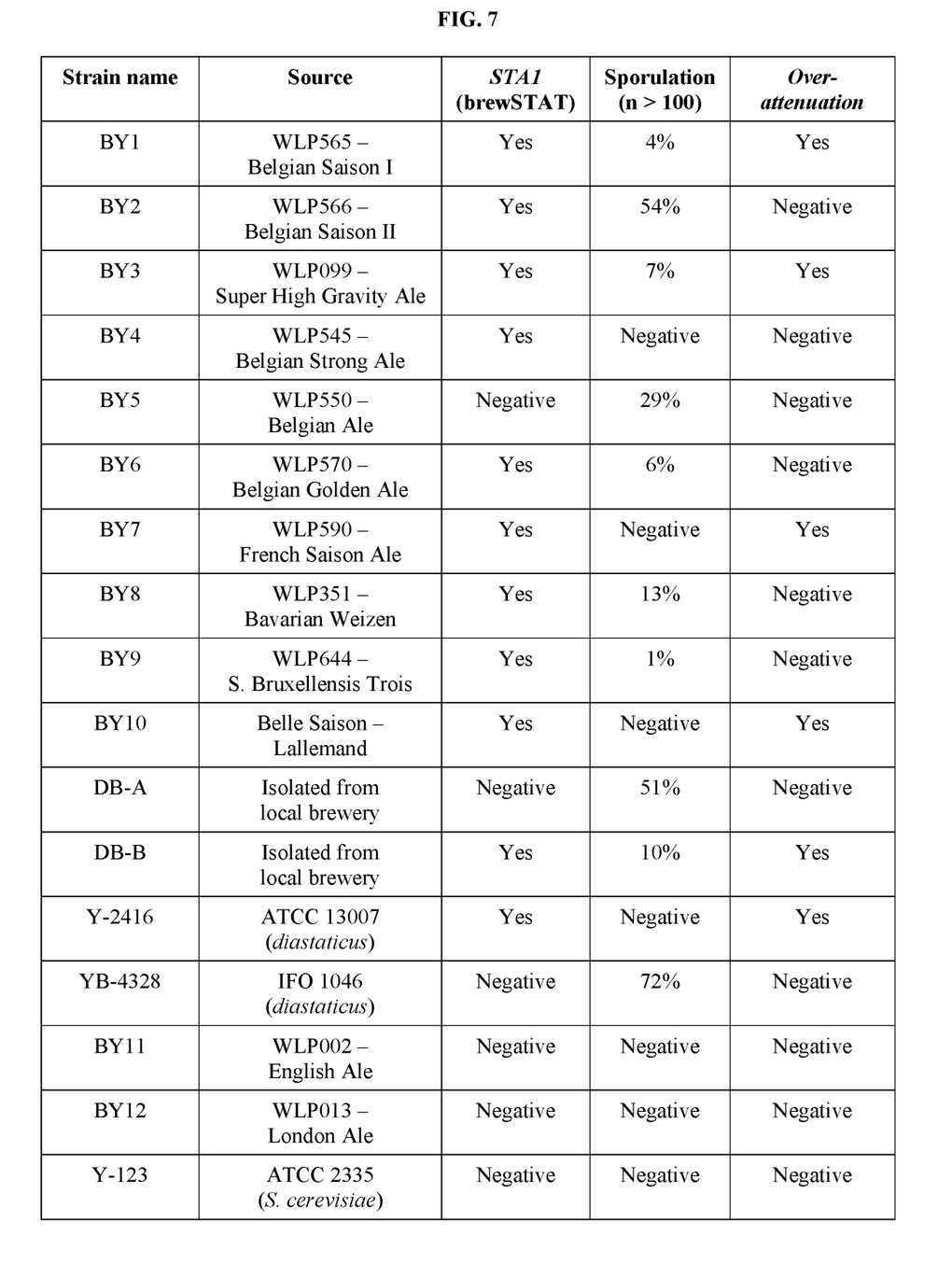
FIG. 7 is a table illustrating strains used and selected results obtained in the present study.

As compared to Y-123, the *S. cerevisiae* control, CS1, Y-2416, and DB-B demonstrated a two-fold increase in re-fermentation. YB-4238 and DB-A resemble *S. cerevisiae*. These results suggest that Y-123, YB-4238, and DB-A utilize the remaining fermentable sugars in the finished beer, while CS1, Y-2416, and DB-B are able to over-attenuate the beer, possibly as a result of glucoamylase activity. Over-attenuation was also characterized for an expanded subset of commercial strains suspected to be *diastaticus* (FIG. 7)

Example 2

CSSM Selectivity for *diastaticus* Strains over *S. cerevisiae* Strains

Because *diastaticus* strains can over-attenuate beer, they pose a significant contamination risk. In order to detect *diastaticus* strain contamination, a *diastaticus* strain selective medium was developed. The novel medium included cupric sulfate and used soluble starch as the carbohydrate source. Growth of various strains was tested on prior art medium Lin's cupric sulfate medium (LCSM) and the novel cupric sulfate starch medium (CSSM) (Table 2 and FIG. 6)).

Figure 3A:
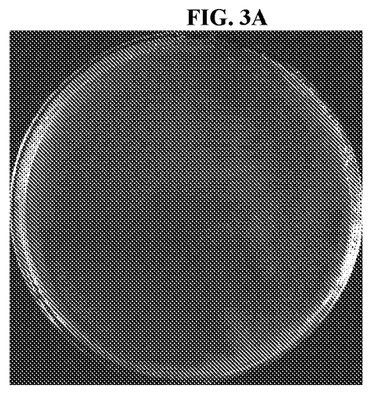
FIGS. 3A-3F are images of culture plates showing yeast growth on Lin's Cupric Sulfate Medium (LCSM) and Cupric Sulfate Starch Medium (CSSM). *Cerevisiae* strain Y-123 (FIGS. 3A-3B), *diastaticus* strain YB-4238 (FIGS. 3C-3D), and *diastaticus* strain DB-B (FIGS. 3E-3F) were plated on LCSM (FIGS. 3A, 3C and 3E) and CSSM (FIGS. 3B, 3D and 3F).
Figure 3B:
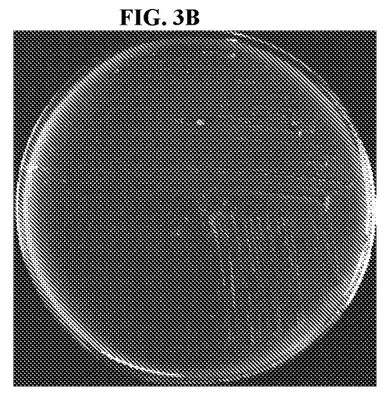
Figure 3C:
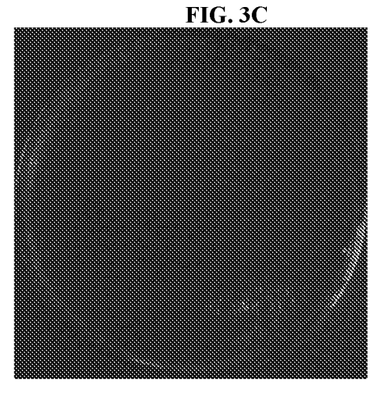
Figure 3D:
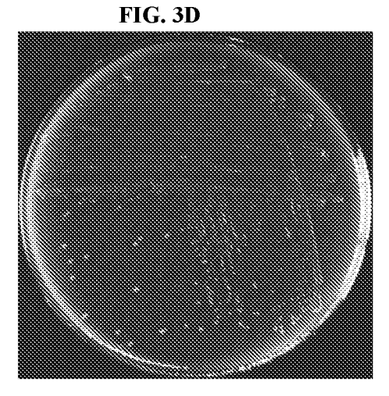
Figure 3E:
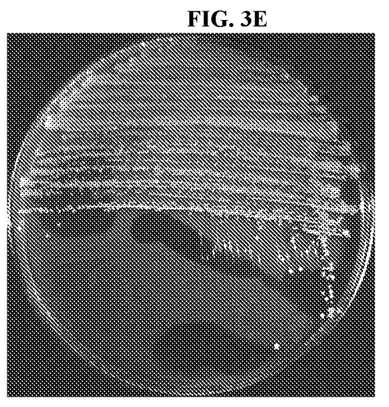
Figure 3F:
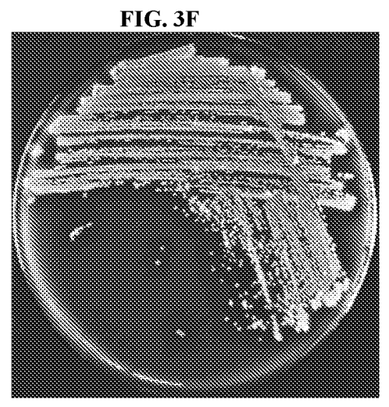

No *S. cerevisiae* strains grew on either LCSM or CSSM. Three of the five *diastaticus* strains grew on LCSM. All five *diastaticus* strains grew on CSSM but exhibited variable growth. DB-B and CS1 demonstrated strong growth, while DB-A, Y-2416, and YB-4238 exhibited delayed growth and smaller colonies. Representative plates are shown in FIGS. 3A-3F. In addition DB-B and CS1 exhibited zones of clearing on the CSSM plates indicative of robust starch hydrolysis (FIG. 3F).

In an expanded subset of commercial brewer's yeast suspected to be *diastaticus*, most yeast which were STA1+, as indicated by the BrewSTAT, were capable of growth on CSSM with variable or negative growth on LCSM (FIG. 6). BY5 demonstrated negative growth on LCSM and CSSM, was STA1 negative, did not over-attenuate, and did not sporulate. BY5 is likely not a *diastaticus* strain.

Example 3

Identification of *diastaticus* Strains Via PCR

Traditional identification of yeast involves sequencing of the 28S rRNA gene. Unfortunately, this region is ineffective at identification of *diastaticus* due to its 100% identity with typical brewer's yeast. Yamauchi et al. have demonstrated that PCR of the STA1 gene enables differentiation of *diastaticus* strains over other brewing microorganisms including species of *Saccharomyces*, *Brettanomyces*, *Lactobacillus*, and numerous wild yeast (Yamauchi et al. Journal of the American Society of Brewing Chemists. 1998; 56(2):58-63.).

Figure 4:
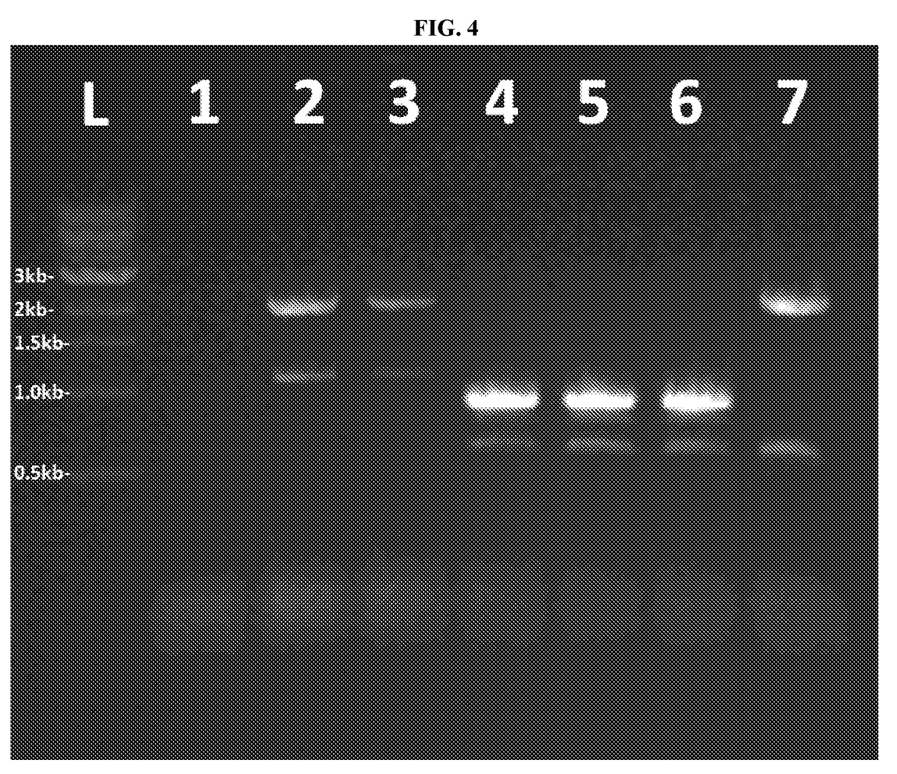
FIG. 4 is an image of a PCR gel showing the specificity of SD-5A and SD-6B primers for the identification of *diastaticus*. Lane L, 1 kb ladder; lane 1, no DNA; lane 2, *S. cerevisiae* Y-123; lane 3, DB-A; lane 4, DB-B; lane 5, *diastaticus* CS-1; lane 6, *diastaticus* Y-2416; lane 7, *diastaticus* YB-4238.

The PCR primers SD5A and SD6B and the PCR conditions first described by Yamauchi et al. were used in this study to confirm the utility of these primers for the identification of *diastaticus*. Successful amplification of the *dia*- staticus STA1 gene results in an 868 base-pair fragment. Strains DB-B, CS1, and Y-2416 showed a strong amplicon at 868 bp, whereas strains Y-123, YB-4238, and DB-A were negative (FIG. 4). The presence of STA1 in suspected *diastaticus* strains was further evaluated (FIG. 7).

Example 4

CSSM Selectivity for *diastaticus* Contamination in Yeast Slurries

One of the rising concerns with *diastaticus* in the brewery is the difficulty in detecting mild contamination in a yeast slurry. In this scenario, fermentation will often persist as normal with no appreciable changes in performance or beer quality pre-packaging. In addition, contamination is often very low and can be difficult to detect given the abundance of brewer's yeast. Problems may only start to manifest in unfiltered, packaged beer; where brewer's yeast has ceased fermentation, but *diastaticus* can utilize dextrins through glucoamylase activity.

Figure 5A:
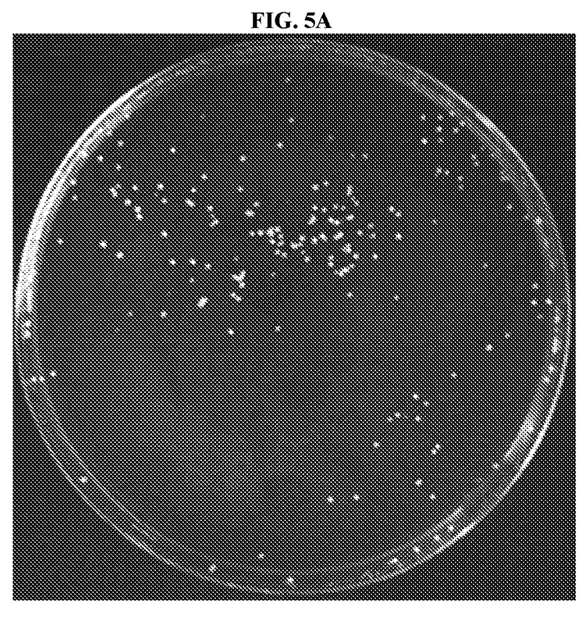
FIGS. 5A-5B are images of culture plates showing detection of *diastaticus* contamination in a yeast slurry. A 1:1000 dilution of *diastaticus* to *S. cerevisiae* cells was plated on CSSM after 0 hr (FIG. 5A) and 48 hr (FIG. 5B) incubation.
Figure 5B:
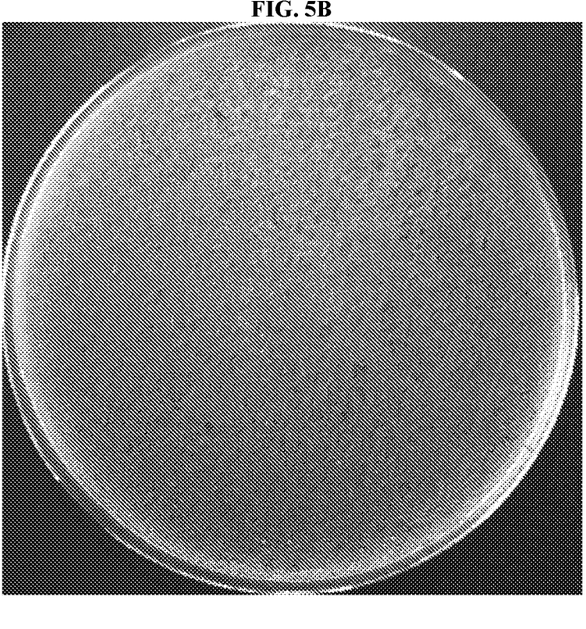

To evaluate the ability of CSSM to select for *diastaticus* contamination in yeast slurries, a 1:1000 culture of *diastaticus* to ale yeast was created. This culture was then enriched in CSSM broth. The original 1:1000 slurry and the CSSM enrichment were plated on YPD and CSSM agar for comparison. Detection of *diastaticus* on a general media like YPD is impossible due to the overabundance of the ale yeast. However, the use of CSSM allowed for only *diastaticus* to be selected (FIGS. 5A-5B). Furthermore, enrichment of the contaminated slurry in CSSM broth lead to an overabundance of *diastaticus* yeast.

Example 5

Sporulation of *diastaticus* Strains

The spoilage capability of any microorganism is exacerbated by its ability to sporulate and thus survive harsh conditions such as beer, CIP chemicals, environmental biofilms, and even pasteurization. *Diastaticus* strains were evaluated for their ability to sporulate on a variety of different media. All *diastaticus* strains except for CS1 exhibited the ability to form endospores (Table 3). CS1 and *S. cerevisiae* Y-123 did not sporulate.

Figure 8:
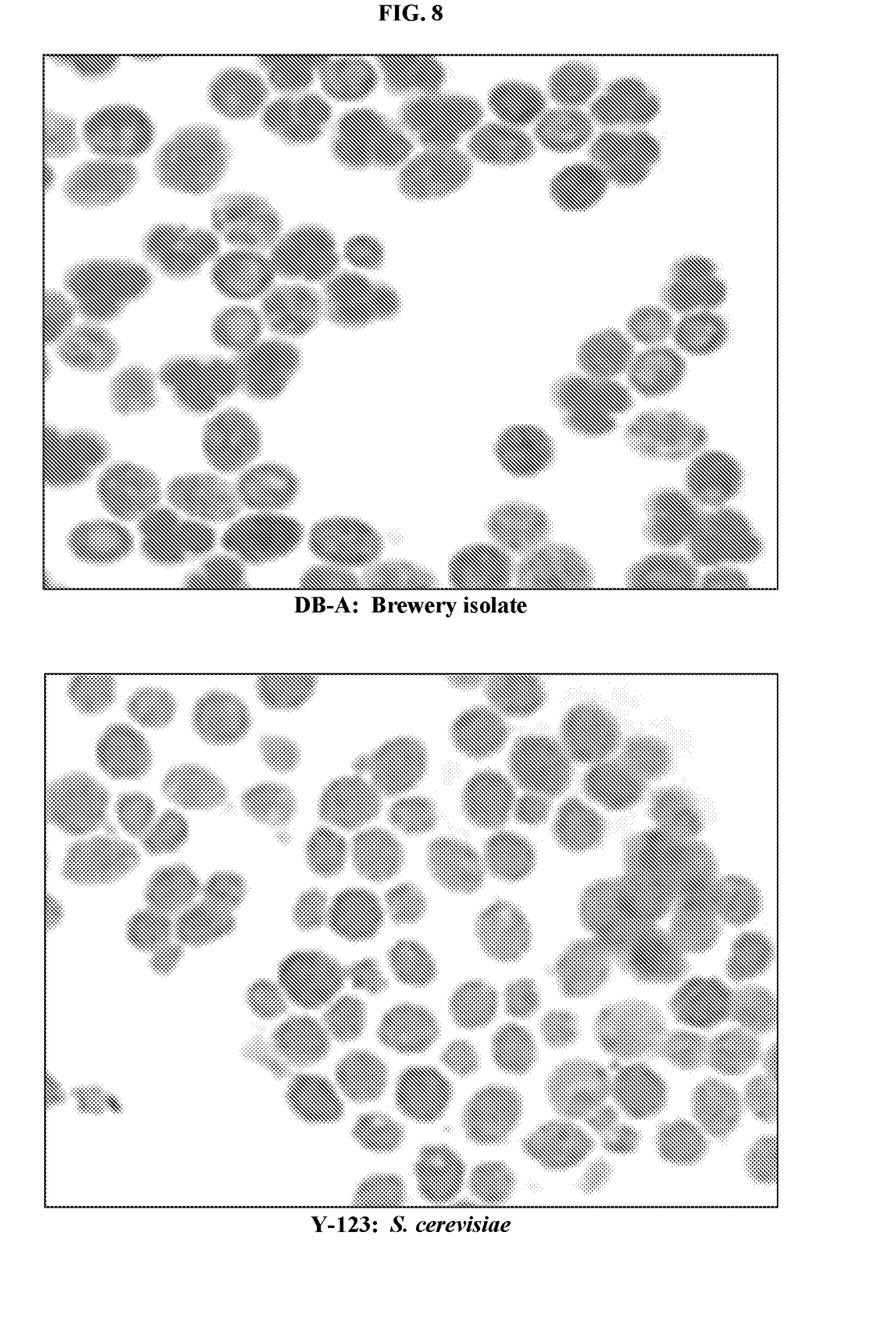
FIG. 8 illustrates results relating to sporulation ability of *diastaticus* strains on acetate agar. Spores were stained with malachite green and safranin-O.

Each strain was cultured on acetate agar, cornmeal agar, malt extract (ME) agar, V8 agar, and yeast and mold (YM) agar. The plates were incubated at 25° C. for 10 days. A spore stain was then performed using malachite green as the primary stain and Safranin-O as the counterstain. (+) indicates presence of blue-stained spores while (−) indicates lack of staining or spores (FIG. 8).

TABLE 3

Sporulation ability of *diastaticus* strains.

| Strain | Acetate | Cornmeal | ME | V8 | YM |
|---|---|---|---|---|---|
| DB-A | + | + | + | + | + |
| DB-B | + | − | − | + | + |
| Belle Saison | − | − | − | − | − |
| Y-2416 | + | − | − | − | + |
| YB-4238 | + | − | + | + | + |
| Y-123 | − | − | − | − | − |

Based on the results in Table 3, acetate agar was used to evaluate the sporulation capabilities of the expanded commercial yeast strains suspected of being *diastaticus* (FIG. 7). Different *diastaticus* strains demonstrate variable abilities to sporulate.

Example 6

Differences Between *diastaticus* Spoilage Strains

As compared to other *diastaticus* strains, CS1 demonstrated robust growth on CSSM with zones of starch clearing, yet it did not sporulate like the other *diastaticus* strains. Without wishing to be limited to any particular theory, this may be due to the historic domestication of CS1 as a brewing strain. Selection of positive brewing traits, like high attenuation displayed by CS1, may have been the result of past gene duplication events. Such gross genomic changes typically render a yeast unable to sporulate due to aneuploidy. These results emphasize that a difference exists between "domesticated *diastaticus*" and wild *diastaticus* strains in starch utilization, sporulation, and over-attenuation. Because a domesticated *diastaticus* strain like CS1 cannot sporulate, it represents less of a spoilage threat than wild *diastaticus* species. All wild *diastaticus* strains studied sporulated on Acetate Agar (Table 3).

In addition to differences between domesticated and wild *diastaticus* strains, there exists heterogeneity between the wild *diastaticus* strains. While all but CS1 were capable of forming endospores, their strength of growth on CSSM was variable. Interestingly, DB-A and Y4328, both known beer spoilers, exhibited weak growth on CSSM. These two strains also tested negative for STA1 (FIG. 4) and did not over-attenuate beer like the other *diastaticus* strains, more so resembling the *S. cerevisiae* control (FIG. 2). By comparing the expanded subset of suspected *diastaticus* yeasts, there is a varying degree or ability to sporulate and over-attenuate. However all yeasts that tested positive for STA1 were also capable of growing on CSSM, unlike LCSM. The wild brewery isolate DB-A tested negative for STA1 but was capable of growing on CSSM. This indicates that additional genes may be used for starch utilization, and such strains can grow on CSSM.

Figure 9:
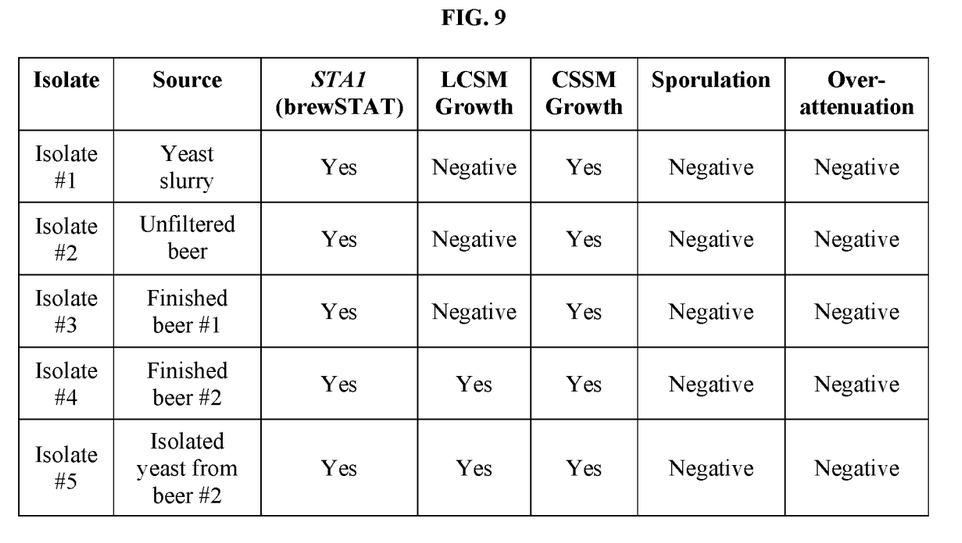
FIG. 9 is a table illustrating results relating to isolation of STA+, LCSM(−) strains in commercial beer.

Samples from a commercial brewery tested positive for the presence of STA1 via PCR test but did not yield colonies on LCSM (FIG. 9). Three such samples, collected from a yeast slurry, unfiltered beer, and finished beer, yielded positive growth on CSSM. Colonies from each sample tested positive for STA1 but were negative in their ability to sporulate and over-attenuate. These results demonstrate the ability of CSSM to isolate *diastaticus* yeasts as compared to LCSM (FIG. 9)

Enumerated Embodiments

The following enumerated embodiments are provided, the numbering of which is not to be construed as designating levels of importance:

Embodiment 1 provides a yeast culture medium composition comprising yeast extract, peptone, cupric sulfate, potassium phosphate, ammonium chloride, water, and at least one carbohydrate selected from the group consisting of starch, dextrin, and any combinations thereof.

Embodiment 2 provides the composition of Embodiment 1, consisting essentially of yeast extract, peptone, cupric sulfate, potassium phosphate, ammonium chloride, water, and at least one carbohydrate selected from the group consisting of starch, dextrin, and any combinations thereof.

Embodiment 3 provides the composition of Embodiment 1, further comprising agar.

Embodiment 4 provides the composition of any of Embodiments 1 and 3, which comprises about 10 g/L of yeast extract.

Embodiment 5 provides the composition of any of Embodiments 1 and 3-4, which comprises about 20 g/L of peptone.

Embodiment 6 provides the composition of any of Embodiments 1 and 3-5, which comprises about 20 g/L of the at least one carbohydrate.

Embodiment 7 provides the composition of any of Embodiments 1-6, which comprises about 1.0 g/L to about 2.5 g/L of cupric sulfate.

Embodiment 8 provides the composition of any of Embodiments 1-7, which comprises about 1.8 g/L of cupric sulfate.

Embodiment 9 provides the composition of any of Embodiments 1-8, which comprises about 1.0 g/L to about 1.5 g/L of potassium phosphate.

Embodiment 10 provides the composition of any of Embodiments 1-9, which comprises about 1.1 g/L of potassium phosphate.

Embodiment 11 provides the composition of any of Embodiments 1-10, which comprises about 0.5 g/L of ammonium chloride.

Embodiment 12 provides the composition of any of Embodiments 1 and 3-11, which comprises about 20 g/L of agar.

Embodiment 13 provides the composition of any of Embodiments 1-12, which comprises about 10 g/L of yeast extract, about 20 g/L of peptone, about 20 g/L of the at least one carbohydrate, about 1.8 g/L of cupric sulfate, about 1.1 g/L of potassium phosphate, and about 0.5 g/L of ammonium chloride.

Embodiment 14 provides the composition of any of Embodiments 1 and 3-13, which further comprises about 20 g/L of agar.

Embodiment 15 provides the composition of any of Embodiments 1-14, which comprises an amount of cupric sulfate sufficient to promote growth of *Saccharomyces cerevisiae* var. *diastaticus* while inhibiting growth of at least one other variety of brewing yeast.

Embodiment 16 provides the composition of any of Embodiments 1-15, which comprises an amount of starch sufficient to promote growth of *Saccharomyces cerevisiae* var. *diastaticus* while inhibiting growth of at least one other variety of brewing yeast.

Embodiment 17 provides the composition of any of Embodiments 1-16, which comprises an amount of dextrin sufficient to promote growth of *Saccharomyces cerevisiae* var. *diastaticus* while inhibiting growth of at least one other variety brewing yeast.

Embodiment 18 provides the composition of any of Embodiments 15-17, wherein the at least one other variety of brewing yeast comprises *Saccharomyces cerevisiae, Saccharomyces pastorianus, Brettanomyces bruxellensis, Brettanomyces claussenii, Brettanomyces lambicus*, or *Brettanomyces anomalus*.

Embodiment 19 provides the composition of any of Embodiments 1-18, further comprising at least one strain of yeast.

Embodiment 20 provides the composition of any of Embodiments 1-19, further comprising at least one strain of *Saccharomyces cerevisiae*.

Embodiment 21 provides the composition of any of Embodiments 1-20, further comprising at least one strain of *Saccharomyces cerevisiae* var. *diastaticus*.

Embodiment 22 provides a method of culturing yeast, the method comprising incubating a yeast strain in the composition of any of Embodiments 1-21.

Embodiment 23 provides the method of Embodiment 22, wherein the yeast strain comprises at least one strain of *Saccharomyces cerevisiae*.

Embodiment 24 provides the method of any of Embodiments 22-23, wherein the yeast strain comprises at least one strain of *Saccharomyces cerevisiae* var. *diastaticus*.

Embodiment 25 provides the method of any of Embodiments 22-24, wherein the yeast strain is cultured at a temperature of about 20° C. to about 35° C.

Embodiment 26 provides the method of any of Embodiments 22-25, wherein the yeast strain is first propagated in a first culture medium before incubating in the composition of any of Embodiments 1-21.

Embodiment 27 provides the method of any of Embodiments 22-26, wherein the first culture medium comprises yeast extract peptone dextrose.

Embodiment 28 provides the method of any of Embodiments 22-27, wherein the yeast strain is derived from a sample selected from the group consisting of a yeast slurry, a fermenting wort, a beer, a malted beverage and an environmental swab.

Embodiment 29 provides the method of any of Embodiments 22-28, wherein, if the yeast strain grows, propagates, and/or proliferates in the composition, the yeast strain is a strain of *Saccharomyces cerevisiae* var. *diastaticus*.

Embodiment 30 provides the method of any of Embodiments 22-29, wherein, if the yeast strain does not significantly grow, propagate, and/or proliferate in the composition, the yeast strain is not a strain of *Saccharomyces cerevisiae* var. *diastaticus*.

Embodiment 31 provides the method of Embodiment 30, wherein the yeast strain that is not a strain of *Saccharomyces cerevisiae* var. *diastaticus* comprises *Saccharomyces cerevisiae, Saccharomyces pastorianus, Brettanomyces bruxellensis, Brettanomyces claussenii, Brettanomyces lambicus*, or *Brettanomyces anomalus*.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A yeast culture medium composition consisting of:
   yeast extract,
   peptone,
   cupric sulfate,
   potassium phosphate,
   ammonium chloride,
   water, and
   at least one carbohydrate selected from the group consisting of starch, dextrin, and any combinations thereof.

2. The yeast culture medium composition of claim 1, wherein at least one of the following applies:
   (a) the concentration of the yeast extract is about 10 g/L;
   (b) the concentration of the peptone is about 20 g/L;
   (c) the concentration of the at least one carbohydrate is about 20 g/L;

(d) the concentration of the cupric sulfate ranges from about 1.0 g/L to about 2.5 g/;
(e) the concentration of the cupric sulfate is about 1.8 g/L;
(f) the concentration of the potassium phosphate ranges from about 1.0 g/L to about 1.5 g/L;
(g) the concentration of the potassium phosphate is about 1.1 g/L;
(h) the concentration of the ammonium chloride is about 0.5 g/L.

3. A yeast culture medium composition consisting of:
agar,
yeast extract,
peptone,
cupric sulfate,
potassium phosphate,
ammonium chloride,
water, and
at least one carbohydrate selected from the group consisting of starch, dextrin, and any combinations thereof.

4. The composition of claim 3, wherein at least one of the following applies:
(a) the concentration of the yeast extract is about 10 g/L;
(b) the concentration of the peptone is about 20 g/L;
(c) the concentration of the at least one carbohydrate is about 20 g/L;
(d) the concentration of the cupric sulfate ranges from about 1.0 g/L to about 2.5 g/L;
(e) the concentration of the cupric sulfate is about 1.8 g/L;
(f) the concentration of the potassium phosphate ranges from about 1.0 g/L to about 1.5 g/L;
(g) the concentration of the potassium phosphate is about 1.1 g/L;
(h) the concentration of the ammonium chloride is about 0.5 g/L;
the concentration of the agar is about 20 g/L.

5. A yeast culture medium composition comprising:
yeast extract,
peptone,
cupric sulfate,
potassium phosphate,
ammonium chloride,
water, and
starch,
wherein the starch is the sole carbon source in the composition.

6. The composition of claim 5, wherein the composition further comprises agar.

7. A yeast culture medium composition comprising:
about 10 g/L of yeast extract,
about 20 g/L of peptone,
about 20 g/L of the at least one carbohydrate selected from the group consisting of starch, dextrin, and any combinations thereof,
about 1.8 g/L of cupric sulfate,
about 1.1 g/L of potassium phosphate, and
about 0.5 g/L of ammonium chloride.

8. The yeast culture medium composition of claim 7, which further comprises about 20 g/L of agar.

9. A mixture consisting of the yeast culture medium composition of claim 1 and at least one strain of yeast.

10. The mixture of claim 9, wherein the at least one strain of yeast is *Saccharomyces cerevisiae*.

11. The mixture of claim 9, wherein the at least one strain of yeast is *Saccharomyces cerevisiae* var. *diastaticus*.

12. A method of culturing yeast, the method comprising incubating a yeast strain in the composition of claim 1.

13. The method of claim 12, wherein the yeast strain comprises at least one strain of *Saccharomyces cerevisiae*.

14. The method of claim 12, wherein the yeast strain comprises at least one strain of *Saccharomyces cerevisiae* var. *diastaticus*.

15. The method of claim 12, wherein the yeast strain is cultured at a temperature of about 20° C. to about 35° C.

16. The method of claim 12, wherein the yeast strain is first propagated in a first culture medium before incubating in the composition of claim 1.

17. The method of claim 16, wherein the first culture medium comprises yeast extract peptone dextrose.

18. The method of claim 12, wherein the yeast strain is derived from a sample selected from the group consisting of a yeast slurry, a fermenting wort, a beer, a malted beverage and an environmental swab.

19. The method of claim 12, wherein, if the yeast strain grows, propagates, or proliferates in the composition, the yeast strain is a strain of *Saccharomyces cerevisiae* var. *diastaticus*.

20. The method of claim 12, wherein, if the yeast strain does not significantly grow, propagate, or proliferate in the composition, the yeast strain is not a strain of *Saccharomyces cerevisiae* var. *diastaticus*.

21. The method of claim 20, wherein the yeast strain that is not a strain of *Saccharomyces cerevisiae* var. *diastaticus* comprises *Saccharomyces cerevisiae*, *Saccharomyces pastorianus*, *Brettanymyces bruxilensis*, *Brettanomyces claussenii*, *Brettanomyces lambicus*, or *Brettanomyces anomalus*.

* * * * *